US00PP13897P39

(12) United States Plant Patent
Meilland

(10) Patent No.: US PP13,897 P3
(45) Date of Patent: Jun. 17, 2003

(54) HYBRID TEA ROSE PLANT NAMED 'MEICEPPUS'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 162 days.

(21) Appl. No.: 09/827,935

(22) Filed: Apr. 9, 2001

(65) Prior Publication Data

US 2003/0028933 P1 Feb. 6, 2003

(51) Int. Cl.[7] ..... A01H 5/00
(52) U.S. Cl. ..... Plt./134
(58) Field of Search ..... Plt./134

(56) References Cited

U.S. PATENT DOCUMENTS

PP11,529 P * 9/2000 Ferrer ..... Plt./137

OTHER PUBLICATIONS

UPOV ROM GTITM Computer Database, GTI JOUVE Retrieval Software 2002/02 citations for 'Meifebink'.*
Protection Des Obtentions Vegetales, Bulletin Officel du Comité de la Protection des Obtentions Végétales, No. 3, Title Pages and pp. 116, 119, and 126 (2000).

* cited by examiner

*Primary Examiner*—Bruce R. Campell
*Assistant Examiner*—W C Haas
(74) *Attorney, Agent, or Firm*—Burns, Doane, Swecker & Mathis, L.L.P.

(57) ABSTRACT

A new and distinct variety of Hybrid Tea rose plant is provided which abundantly forms attractive fragrant double blossoms having an old-fashioned appearance that are light yellow-orange in coloration. The plant exhibits a semi-upright growth habit, dense medium green semi-glossy foliage, and very good disease resistance particularly with respect to Black Spot. The attractive medium green foliage contrasts nicely with the light-colored blossoms. The new variety is particularly well suited for growing as attractive ornamentation in the landscape such as in parks and gardens.

1 Drawing Sheet

BOTANICAL/COMMERCIAL CLASSIFICATION

Figures 1, 2, 3, 4, 5, 6, 7, 8, 9, 10, 11, 12, 13, 14, 15:
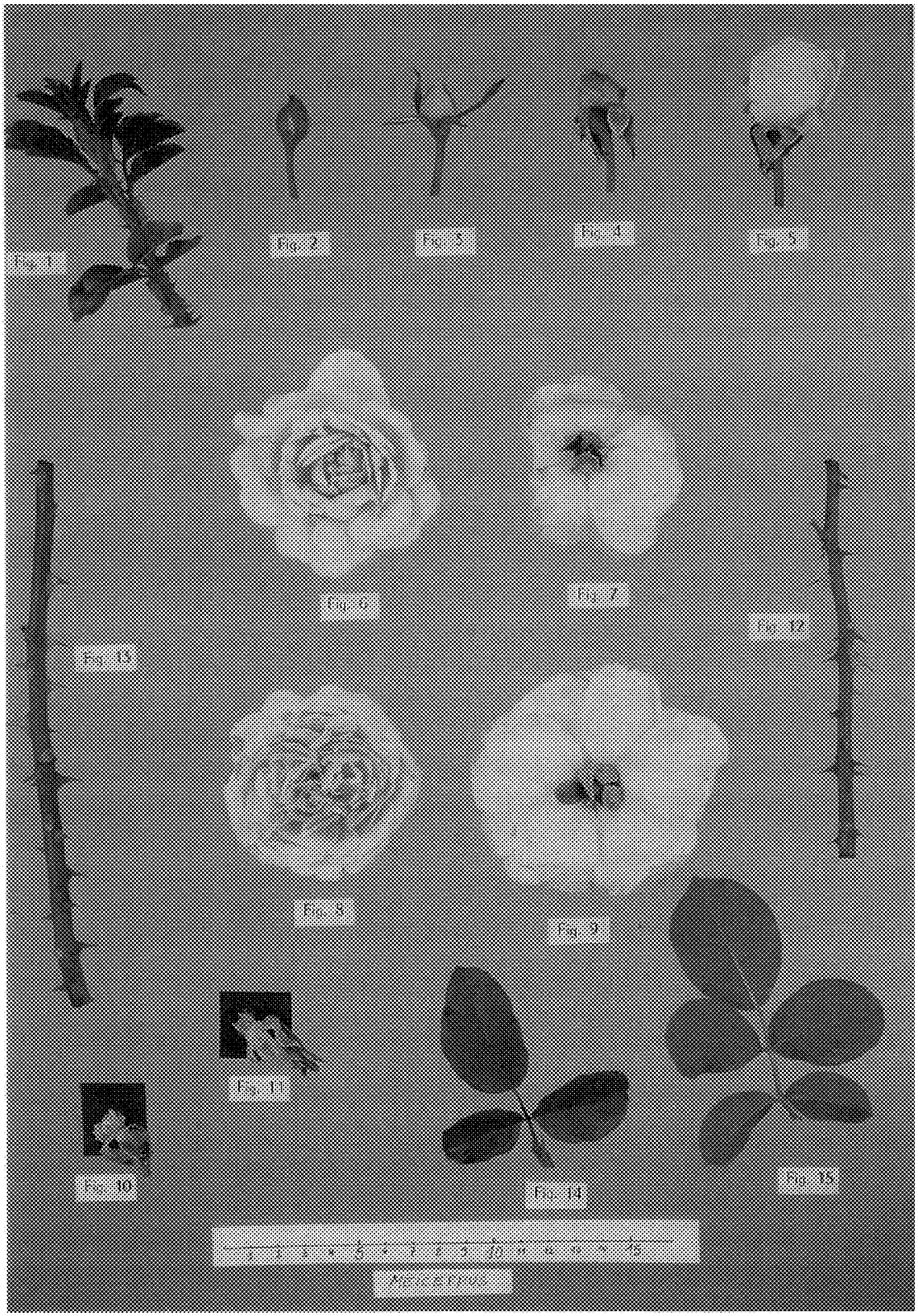

Rosa hybrida / Hybrid Tea Rose Plant.

VARIETAL DENOMINATION cv. 'Meiceppus'.

SUMMARY OF THE INVENTION

The new variety of Rosa hybrida Hybrid Tea rose plant was created by artificial pollination wherein two parents were crossed which previously had been studied in the hope that they would contribute the desired characteristics. The female parent (i.e., the seed parent) of the product of the cross of the 'Meicapinal' variety (non-patented in the United States) and the 'Meirestif' variety (non-patented in the United States). The male parent (i.e., the pollen parent) was the 'Meipsilon' variety (non-patented in the United States). The parentage of the new variety can be summarized as follows:

('Meicapinal'×'Meirestif')×'Meipsilon'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) Exhibits a semi-upright growth habit, (b) Abundantly forms attractive fragrant double blossoms having an old-fashioned appearance that are light yellow-orange in coloration,
(c) Forms dense medium green semi-glossy foliage that contrasts well with the light-colored blossoms,
(d) Exhibits very good resistance to Black Spot, and
(e) Is particularly well suited for growing as attractive ornamentation in the landscape.

The new variety well meets the needs of the horticultural industry and can be grown to advantage in parks and gardens.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meiceppus' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa froebelli* understock and growing in outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface; and FIG. 15—illustrates a specimen of a leaf with five leaflets—plan view—under surface.

DETAILED DESCRIPTION

The chart used in the identification of the colors is that of The Royal Horticultural Society (R.H.S. Colour Chart). The description is based on the observation of one and one-half year-old plants during November while budded on *Rosa froebelli* understock and growing outdoors at Le Cannet des Maures, Var, France. The coloration in more common terms precedes reference to the chart in some instances. Such terminology is to be accorded its ordinary dictionary significance.

Class: Hybrid tea.

Plant:

*Height.*—Approximately 90 to 110 cm at the end of the growing season.

*Habit.*—Semi-upright.

Branches:

*Color.*—Young stems: near Green Group 138A. Adult wood: near Green Group 139A.

*Thorns.*—Size: large (as illustrated). Quantity: moderately numerous (as illustrated). Color: near Greyed-Orange Group 164C on young stems and near Greyed-Orange Group 177A on adult wood. Configuration: oval at the base, concave on the lower side and elongated downwards on the upper side.

Leaves:

*Stipules.*—Adnate, pectinate, and rather broad.

*Petioles.*—Non-glandular, with few prickles and near Yellow-Green Group 146C in coloration.

*Leaflets.*—Number: 3, 5 (most often), and 7. Shape: obtuse at the base with a symmetrical tip. Serration: regular (as illustrated). Texture: consistent. General appearance: very dense, medium green, and semi-glossy. Color (young foliage): upper surface: near Yellow-Green Group 147B and widely suffused with anthocyanin coloration. under surface: near Yellow-Green Group 147B and widely suffused with anthocyanin coloration. Color (adult foliage): upper surface: near Yellow-Green Group 147A. under surface: near Yellow-Green Group 148A.

Inflorescence:

*Number of flowers.*—Usually one flower per stem.

*Peduncle.*—Near Yellow-Green Group 146C in coloration, rigid, medium in size, and the length is approximately 5 cm on average.

*Sepals.*—Upper surface: five in number, tomentose, approximately 2.5 cm in length on average, commonly possess a few extensions (as illustrated), and near Yellow-Green Group 148C in coloration. Under surface: glabrous, and near Yellow-Green Group 146C in coloration and commonly with a few small extensions (as illustrated).

*Buds.*—Shape: conical. Length: approximately 2.5 cm on average. Diameter: approximately 2 cm on average when the sepals are completely open. Color: upper surface: near Yellow-Orange Group 15D with Yellow-Orange Group 15C at the base. under surface: near Yellow-Orange Group 15D with Yellow-Orange Group 15C at the base.

*Flower.*—Shape: cup-shaped. Diameter: approximately 12 to 13 cm on average. Color (when opening begins): upper surface: near Chinese Yellow, Yellow-Orange Group 20D and widely suffused with Orange Buff, Yellow-Orange Group 22C. under surface: near Chinese Yellow, Yellow-Orange Group 20D. Color (when blooming): upper surface: near Chinese Yellow, Yellow-Orange Group 20D, and widely suffused with Orange Buff, Yellow-Orange Group 22C. under surface: near Chinese Yellow, Yellow-Orange Group 20D. Color (at end of opening): upper surface: near Chinese Yellow, Yellow-Orange Group 20D, and widely suffused with Orange Buff, Yellow-Orange Group 22C. under surface: near Chinese Yellow, Yellow-Orange Group 20D. Fragrance: strong. Lasting quality: long on the plant and when cut and placed in a vase. Petal shape: wedge-shaped. Stamen number: approximately 75 on average. Anthers: near Yellow Group 8B in coloration. Filaments: near Red Group 45D in coloration. Styles: near Yellow Group 8B in coloration. Pistils: approximately 108 on average. Receptacle: yellow-green in coloration, and funnel-shaped in longitudinal section.

Development:

*Vegetation.*—Very vigorous and strong.

*Blooming.*—Very abundant.

*Resistance to diseases.*—Very good especially with respect to Black Spot.

*Aptitude to bear fruit.*—None.

*I claim:*

1. A new and distinct variety of Hybrid Tea rose plant characterized by the following combination of characteristics:

(a) Exhibits a semi-erect growth habit, (b) Abundantly forms attractive fragrant double blossoms having an old-fashioned appearance that are light yellow-orange in coloration, (c) Forms dense medium green semi-glossy foliage that contrasts well with the light-colored blossoms, (d) Exhibits very good resistance to Black Spot, and (e) Is particularly well suited for growing as attractive ornamentation in the landscape;

substantially as herein shown and described.

* * * * *

Inches